United States Patent [19]

Hansma et al.

[11] 4,230,889
[45] Oct. 28, 1980

[54] DESENSITIZED SOLUTION OF DIHYDROPEROXYCYCLOHEXANE

[75] Inventors: Hendrik Hansma, Schalkhaar; Arnold Schroeder, Deventer, both of Netherlands

[73] Assignee: Akzona Incorporated, Asheville, N.C.

[21] Appl. No.: 922,145

[22] Filed: Jun. 30, 1978

[30] Foreign Application Priority Data

Jul. 4, 1977 [NL] Netherlands ................... 7707356

[51] Int. Cl.$^3$ ............................ C07C 179/053
[52] U.S. Cl. ........................................ 568/559
[58] Field of Search ............. 260/610 C, 610 SK; 568/559

[56] References Cited

U.S. PATENT DOCUMENTS

| | | | |
|---|---|---|---|
| 3,330,871 | 7/1967 | Mageli et al. | 568/559 |
| 3,449,275 | 6/1969 | Gerritsen et al. | 260/610 C |

FOREIGN PATENT DOCUMENTS

| | | | |
|---|---|---|---|
| 1060857 | 7/1959 | Fed. Rep. of Germany | 568/559 |
| 2028398 | 6/1972 | Fed. Rep. of Germany | 568/559 |
| 7114839 | 8/1972 | Netherlands | 568/559 |
| 7401405 | 4/1974 | Netherlands | 568/559 |
| 7512457 | 4/1977 | Netherlands | 568/559 |
| 1072728 | 6/1967 | United Kingdom | 568/559 |
| 1199744 | 7/1970 | United Kingdom | 568/559 |
| 1256432 | 12/1971 | United Kingdom | 568/559 |
| 1325956 | 8/1973 | United Kingdom | 568/559 |

OTHER PUBLICATIONS

Cosijn et al. "Recuel Trav. Chimiq.", 87 (1968) p. 1264–1271.

*Primary Examiner*—Werren B. Lone
*Attorney, Agent, or Firm*—Francis W. Young; Robert F. Green

[57] ABSTRACT

1,1-dihydroperoxycyclohexane is desensitized by dissolving it in water, an alcohol, an ester or ketoether. The solution can be handled safely. 1,1-dihydroperoxycyclohexane may be used as an initiator in polymerizing ethylenically unsaturated compounds.

9 Claims, No Drawings

DESENSITIZED SOLUTION OF DIHYDROPEROXYCYCLOHEXANE

This invention relates to a stable composition containing a cyclohexanone peroxide and a solvent. The peroxide can be used as an initiator in the polymerization of ethylenically unsaturated compounds such as a polyester of an unsaturated polycarboxylic acid, and an ethylenically unsaturated monomer such as styrene or the like. The invention more particularly relates to a desensitized solution containing a peroxide which does not demix or separate into multiple layers when it is cooled below a temperature of 0° C.

Cyclohexanone peroxides can be prepared by reacting cyclohexanone with hydrogen peroxide. Depending upon the reaction conditions, various compounds may be obtained, such as bis (1-hydroxycyclohexyl)peroxide of the formula

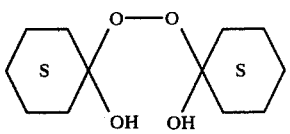   I, 1-hydroxy-1-hydroperoxy-dicyclohexyl peroxide having the formula

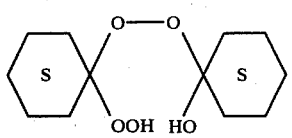   II, or bis (1-hydroperoxycyclohexyl)peroxide having the formula

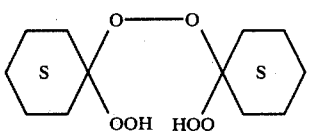   III.

For reasons of safety the above-mentioned compounds, which melt at: 69°–71° C., 78° C., and 82°–83° C., respectively, and are therefore solid at room temperature, can not be marketed as such, but must be desensitized. For instance, besides water-wetted powders also pasty formulations are known in which phthalic esters such as dibutyl phthalate or dimethyl phthalate are mixed with the peroxide as desensitizing agents. These desensitizing agents, however, have little dissolving effect on the cyclohexanone peroxides of the formulae I, II and III above.

Such agents are therefore not suitable for the preparation of safe liquid compositions containing a peroxide in an amount required for them to be commercially acceptable.

The Netherlands Patent Specification No. 102,766 discloses alkyl phosphates as solvents for dicyclohexanone peroxides. Each of the alkyl groups of the alkyl phosphates is to contain not more than 4 carbon atoms. An example of the disclosed phosphates is triethyl phosphate. In the Netherlands specification it is stated that when triethyl phosphate is used as the desensitizing agent at room temperature, 50% solutions of 1-hydroxy-1'-hydroperoxy-dicyclohexyl peroxide (II) can be prepared.

The Netherlands Patent Specification No. 95,259, also describes a concentrated solution. In that case, however, it consists of a mixture of bis(1-hydroxycyclohexyl)peroxide (I) and 1-hydroxy-1'-hydroperoxydicyclohexyl peroxide (II) in triethyl phosphate, with which the particularly favorable solvent power of phosphoric esters for these cyclohexanone peroxides compared with that of phthalic esters is illustrated.

In the German Patent Specification No. 1,060,857 a process is described for the preparation of an oily mixture of various dicyclohexanone peroxides which are not further identified. It is stated in the German specification that unlike pure crystalline dicyclohexanone peroxides this oily mixture is satisfactorily soluble in alcohols, such as methanol, in esters such as dibutyl phthalate, in ketones, such as cyclohexanone, and in hydrocarbons, such as benzene and toluene.

The published German Patent Application No. 2,028,398 describes a powdered composition based on cyclohexanone peroxide and water, in which for the purpose of increasing the solubility in organic liquids there is incorporated a surface active agent in addition to an organic plasticizer-like liquid having a flash point higher than 100° C. and a boiling point higher than 150° C., in which composition the described cyclohexanone peroxide is only slightly soluble.

In the yet unpublished Netherlands Patent Application No. 7,512,457 it is proposed that in order to increase the solubility of 1-hydroxy-1'-hydroperoxy-dicyclohexyl peroxide (II) in organic solvents, water, alkali salts and/or ammonium salts of monocarboxylic acids having 1–18 carbon atoms or of dicarboxylic acids having 2–9 carbon atoms should be mixed with the organic solvent.

In Rec. Trav. Chim. 87 (1968), p. 1264, there is described a process for the preparation of crystalline 1,1-dihydroperoxycyclohexane of the following formula:

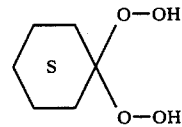   IV

It is an object of this invention to provide a process for stabilizing solid 1,1-dihydroperoxycyclohexane (formula IV) and to provide a desensitized composition containing 1,1-dihydroperoxycyclohexane which can be handled safely in commerce.

Quite in contrast to what a man skilled in the art might expect on the basis of the state of the art or on account of his experience with the crystalline dicyclohexanone peroxides of formulae I, II and III, it has been found surprisingly that 1,1-dihydroperoxycyclohexane of formula IV displays particularly good solubility in non-phosphorus solvents such as water, mono- or polyvalent alcohols, alcohol ethers, keto alcohols, ketoethers and esters derived from an alcohol and monocarboxylic acid or dicarboxylic acid or mixtures of these solvents. The carboxylic acid used in preparing the ester may be an aliphatic or aromatic mono- or polycarboxylic acid. It has been found that upon being cooled below a temperature of 0° C. to say, −20° C., the solutions provided by the invention neither separate into layers nor crystallize out. Accordingly, the invention provides a method for stabilizing 1,1-dihydroperoxycyclohexane (formula IV) by dissolving it in water, an alcohol which may be a monohydric or polyhydric alcohol or an ester of a monohydric or polyhydric alcohol and an aliphatic or aromatic monocarboxylic acid or dicarboxylic acid.

In addition to water, the following compounds are examples of solvents which may be used in the composition provided by the invention:

phthalic esters such as dimethyl phthalte, di-n-butyl phthalate, di-isobutyl phthalate and bis-(2-ethylhexyl) phthalate, and the like;

adipic esters such as dimethyl adipate and the like;

acetic esters such as ethyl acetate, n-butyl acetate, isobutyl acetate, n-amyl acetate, isoamyl acetate and the like;

monohydric alcohols such as n-butanol, isobutanol and the like, and glycols such as ethylene glycol, propylene glycol, diethylene glycol, dipropylene glycol, hexylene glycol, tetra- and hexamethylene glycol and the like;

ether alcohols and glycols such as 2-methoxy-ethanol, 2-ethoxyethanol, diethylene glycol, dipropylene glycol and the like, and their monoethers;

ketoalcohols such as diacetone alcohol and the like; and ketoethers such as 4-methoxy-4-methyl-2-pentanone and the like.

Optionally, binary or ternary mixtures of these solvents may be used.

If desired, diluents, thickeners, if viscous, pasty or kneadable compositions are desired, film-forming agents such as nitrocellulose, stabilizers and internal dyes or pigments, which may serve as mixing indicators in the preparation of homogeneous mixtures may be added. Also there may optionally be added to the solutions other suitable peroxidic compounds or formulations such as hydrogen peroxide.

The content of 1,1-dihydroperoxycyclohexane in compositions provided by the invention may vary between wide limits. Preference is given to compositions which contain from about 9 to about 60% by weight of 1,1-dihyroperoxycyclohexane, which corresponds to an active oxygen content of about 2 to about 13% by weight. Preferred compositions of the invention may contain about 9 to about 60% by weight of 1,1-dihydroperoxycyclohexane, up to about 5% by weight of bis(1-hydroperoxycyclohexyl)peroxide, 0.1 to 10% by weight of $H_2O_2$ and 25 to 70% by weight of a solvent.

The compositions provided by the invention are suitable to be used in chemical reactions taking place under the influence of free radicals. The composition of the invention in combination with compounds acting as accelerators, such as salts derived from transition metals, for instance Fe, Mn, Co, vanadium, Ce, and the like, and inorganic or organic acids are particularly suitable to be used as an initiator in the curing of mixtures of unsaturated polyester resins and suitable monomers. By "unsaturated polyester resins" as used herein is meant the condensation products of mixtures of maleic anhydride and a polyvalent aliphatic and/or aromatic carboxylic acid or anhydride derived thereform, such as phthalic anhydride, and diethylene glycol or dipropylene glycol or mixtures of these diols.

Examples of suitable copolymerizable monomers are styrene, divinyl benzene, methyl-(meth)acrylate, vinyl acetate, diallylphthalate, triallyl-isocyanurate, N-vinyl pyrrolidone, alkyl-diglycol carbonate, trimethylol propane mono- and diallyl ether.

The invention is further described in the following illustrative examples.

EXAMPLE 1

A commercial composition of bis(1-hydroxycyclohexyl) peroxide containing 90% by weight of the peroxide of formula I, 0.08% by weight of $H_2O_2$ and about 10% by weight of water (active oxygen content 6.3% by weight) was added, with stirring, in such a large amount to dimethylterephthalate over a period of one hour and at a temperature of 20° C. that after this period a considerable amount of undissolved material was still present.

This undissolved material was subsequently filtered off at 20° C. The active oxygen content of the resulting saturated solution was determined. From this content the solubility of bis(1-hydroxycyclohexyl)peroxide in dimethylphthalate at 20° C. was calculated.

Likewise, the solubility of bis(1-hydroxycyclohexyl) peroxide in other solvents was measured both at +20° C. and at −20° C. The results obtained are listed in Table A.

EXAMPLE 2

A commercial composition of 1-hydroperoxy-1'-hydroxydicyclohexyl peroxide containing 91% by weight of the peroxide having formula II, 0.04% by weight of $H_2O_2$ and about 9% by weight of water (active oxygen content 11.85% by weight) was added, with vigorous stirring, in such a large amount to dimethylphthalate over a period of one hour at 22° C. that after this period a considerable amount of undissolved material was still present. This undissolved material was subsequently filtered off at 22° C. Of the resulting saturated solution the active oxygen content was determined.

And from this content the solubility of 1-hydroperoxy-1'-hydroxydicyclohexyl peroxide in dimethylphthalate at 22° C. was calculated.

Likewise, the solubility of 1-hydroperoxy-1'-hydroxydicyclohexyl peroxide was measured in other solvents both at +22° C. and at −22° C. The results obtained in this example are listed in Table A.

EXAMPLE 3

A commercial composition of bis(1-hydroperoxycyclohexyl) peroxide containing 97% by weight of the peroxide of formula III, 0.06% by weight of $H_2O_2$, 1.5% by weight of 1-hydroperoxy-1'-hydroxydicyclohexyl peroxide, 0.5% by weight of a cyclic dimer cyclohexanone peroxide, and <1% by weight of water (active oxygen content of 18.0% by weight) was added, with vigorous stirring, in such a large amount to dimethyl phthalate over a period of one hour at 20° C., that after this period a considerable amount of undissolved material was still present. This undissolved material was subsequently filtered off at 20° C. Of the resulting saturated solution the content of active oxygen was determined. For this content the solubility of bis(1-hydroperoxycyclohexyl)peroxide in dimethylphthalate at 20° C. was calculated.

Likewise, the solubility of bis(1-hydroperoxycyclohexyl) peroxide in other solvents was measured both at +20° C. and at −20° C. The results obtained are listed in Table A.

EXAMPLE 4

100 grams of a 43% by weight solution in diethyl ether of 1,1-dihydroperoxycyclohexane were homogeneously mixed with about 40 grams of dimethyl phthalate. The ether was evaporated off from the mixture under reduced pressure at a temperature not exceeding 20° C. The resulting solution of 1,1-dihydroperoxycyclohexane in dimethylphthalate contained about 50% by weight of this peroxide of formula IV. After a few week's storage at 20° C. the solution showed no crystallization phenomena.

Likewise, measurements were carried out on solutions of this peroxide in other solvents both at +20° C. and at −20° C. The results of these measurements are given in Table A.

EXAMPLE 5

To 120 grams of a solution in diethyl ether of 40.0% by weight of 1,1-dihydroperoxycyclohexane, 0.96% by weight of bis(1-hydroperoxycyclohexyl)peroxide, 0.075% by weight of $H_2O_2$ and 4.8% by weight of water there were added 50.7 grams of n-butyl acetate. Subsequently, the ether was distilled off under reduced pressure. The yield was 105.7 grams of a peroxidic solution in n-butyl acetate containing active oxygen in an amount of 10.0% by weight, 45.4% by weight of 1,1-dihydroperoxycyclohexane, and about 48% by weight of n-butyl acetate.

Upon prolonged storage at 0° C. and −20° C. this solution displayed no demixing or crystallization phenomena.

To 30 grams of this solution there were added 15.4 grams of n-butyl acetate and 45.4 grams of a 30% by weight solution of nitrocellulose in n-butyl acetate. The yield was a crystal clear liquid an active oxygen content of 3.2% by weight which after 8 weeks' storage at 20° C. did not show any change in clarity or active oxygen content.

Although the invention has been described in detail for the purpose of illustration, it is to be understood that such detail is solely for that purpose and that variations can be made therein by those skilled in the art without departing from the spirit and scope of the invention except as it may be limited by the claims.

What is claimed is:

1. A stable composition containing a cyclohexanone peroxide and a solvent, characterized in that the peroxide contained in the composition is a cyclohexanone peroxide consisting essentially of 1,1-dihydroperoxycyclohexane and the solvent contained in it is water; a mono- or polyhydric alcohol; an alcohol ether; an ester derived from an aliphatic or aromatic monocarboxylic acid or polycarboxylic acid and a monohydric or polyhydric alcohol; a ketoalcohol or a ketoether.

2. The composition of claim 1, characterized in that it contains at least 9% by weight of 1,1-dihydroperoxycyclohexane.

3. The composition of claim 1, characterized in that it contains a diluent, a thickener, a film-forming agent, a stabilizer, a dye and/or a pigment.

4. A method for desensitizing solid 1,1-dihydroperoxycyclohexane which comprises dissolving it in water, an alcohol, an ester or keotoether.

5. The method of claim 4 wherein the alcohol is a monohydric or polyhydric alcohol, an alcohol-ether or a ketoalcohol.

6. A desensitized peroxide composition comprising a solution of 1,1-dihydroperoxycyclohexane in water, an alcohol, an ester or ketoether.

7. The composition of claim 6 wherein the alcohol is a monohydric or polyhydric alcohol, an alcohol ether or ketoalcohol.

8. A method for stabilizing 1,1-dihydroperoxycyclohexane which comprises dissolving it in water, an alcohol, an ester or ketoether.

9. A stable solution containing 1,1-dihydroperoxycyclohexane dissolved in water, an alcohol, an ester or ketoether.

* * * * *

TABLE A

| Solvent | PEROXIDE HAVING FORMULA OF THE NUMBER INDICATED | | | | | | | |
|---|---|---|---|---|---|---|---|---|
| | I | | II | | III | | IV | |
| | °C. | Solubility | °C. | Solubility | °C. | Solubility | °C. | Solubility |
| dimethylphthalate | 20° | 4.4 | 22° | 10.5 | 20° | 15.3 | 20° | >50 |
| dibutylphthalate | 20° | 3.6 | 22° | 7.6 | 20° | 15.5 | 20° | >50 |
| | −20° | 3.4 | −20° | 2.8 | −20° | 7.1 | −20° | >50 |
| bis(2-ethylhexyl) | 20° | 4.9 | 22° | 5.7 | 20° | 11.8 | 20° | >50 |
| phthalate | −20° | 3.4 | −20° | 5.2 | −20° | 7.3 | −20° | 43 |
| n-butyl acetate | 20° | 7.9 | 22° | 20.6 | 20° | 32.8 | 20° | >50 |
| | −20° | 7.6 | −20° | 6.1 | −20° | 11.5 | −20° | 45 |
| n-butyl alcohol | 20° | 28.6 | 22° | 38.3 | 20° | 28.8 | 20° | >50 |
| | −20° | 23.4 | −20° | 5.0 | −20° | 9.0 | −20° | >50 |
| ethylene glycol | 20° | 6.2 | 22° | 10.3 | 20° | 2.3 | 20° | >50 |
| | −20° | 6.3 | −20° | 1.1 | −20° | 1.5 | −20° | 44 |
| 2-methoxyethanol | 20° | 17.1 | 22° | 42.2 | 20° | 36.7 | 20° | >50 |
| | −20° | 16.2 | −20° | 6.9 | −20° | 14.8 | −20° | 44 |
| diacetone alcohol | 20° | 11.7 | 22° | 16.2 | 20° | 35.1 | 20° | >50 |
| | −20° | 11.5 | −20° | 5.3 | −20° | 13.8 | −20° | >50 |
| Water | 20 | <1 | 20 | <1 | 20 | <1 | 20 | >50 |